United States Patent [19]
DeSantis, Jr. et al.

[11] Patent Number: 5,627,209
[45] Date of Patent: May 6, 1997

[54] USE OF CERTAIN 9-HALOPROSTAGLANDINS TO TREAT GLAUCOMA AND OCULAR HYPERTENSION

[75] Inventors: Louis DeSantis, Jr., Fort Worth; Verney L. Sallee, Burleson, both of Tex.

[73] Assignee: Alcon Laboratories, Inc., Fort Worth, Tex.

[21] Appl. No.: 548,257

[22] Filed: Oct. 25, 1995

Related U.S. Application Data

[63] Continuation of Ser. No. 167,747, Dec. 15, 1993, abandoned.

[51] Int. Cl.⁶ .......................... A61K 31/215; A61K 31/19
[52] U.S. Cl. .......................... 514/530; 514/575; 514/913
[58] Field of Search .................................. 514/530, 575, 514/913

[56] References Cited

U.S. PATENT DOCUMENTS

| | | |
|---|---|---|
| 5,004,752 | 4/1991 | Raduechel et al. . |
| 5,093,329 | 3/1992 | Woodward . |

FOREIGN PATENT DOCUMENTS

| | | |
|---|---|---|
| 299914 | 7/1988 | European Pat. Off. . |
| 0561073A1 | 9/1993 | European Pat. Off. . |
| 4229048A1 | 3/1994 | Germany . |
| 4229050A1 | 3/1994 | Germany . |
| 4229051A1 | 3/1994 | Germany . |
| WO90/02553 | 3/1990 | WIPO . |

OTHER PUBLICATIONS

Braun, et al., "Effect of ZK 110.841 on Cerebral Vascular Contraction and $TXA_2$–Release Caused by Thrombin–Stimulated Platelets." *Archives of Pharmacology*, 339 Suppl:R37(148) (1989).

Ney, "Potent Inhibition of FMLP–Induced Neutrophil Activation by the $PGD_2$ Analogue ZK 110.841." *Archives of Pharmacology*, 339 Suppl:R38(150) (1989).

"New Research Drug DLO/8149" Drug License Opportunities (IMSWORLD Publications) (Jun. 25, 1990).

Nakajima et al., *Graefe's Arch. Clin. Exp. Ophthalmol.*, 229:411–413 (1991).

Crawford et al., *J. Glaucoma*, 1:94–99 (1992).

Woodward et al., *Invest. Ophthalmol. Vis. Sci.*, 31:138–146 (1990).

Goh, et al., *Graefe's Arch. Clin. Exp. Ophthalmol.*, 227:476–481 (1989).

Goh, et al. *Jpn. J. Ophthalmol.*, 32:471–480 (1988).

*Primary Examiner*—Zohreh Fay
*Attorney, Agent, or Firm*—James A. Arno; Barry L. Copeland

[57] ABSTRACT

9-Haloprostaglandins are useful in the treatment of glaucoma and ocular hypertension. Also disclosed are ophthalmic, pharmaceutical compositions comprising such prostaglandins.

7 Claims, 1 Drawing Sheet

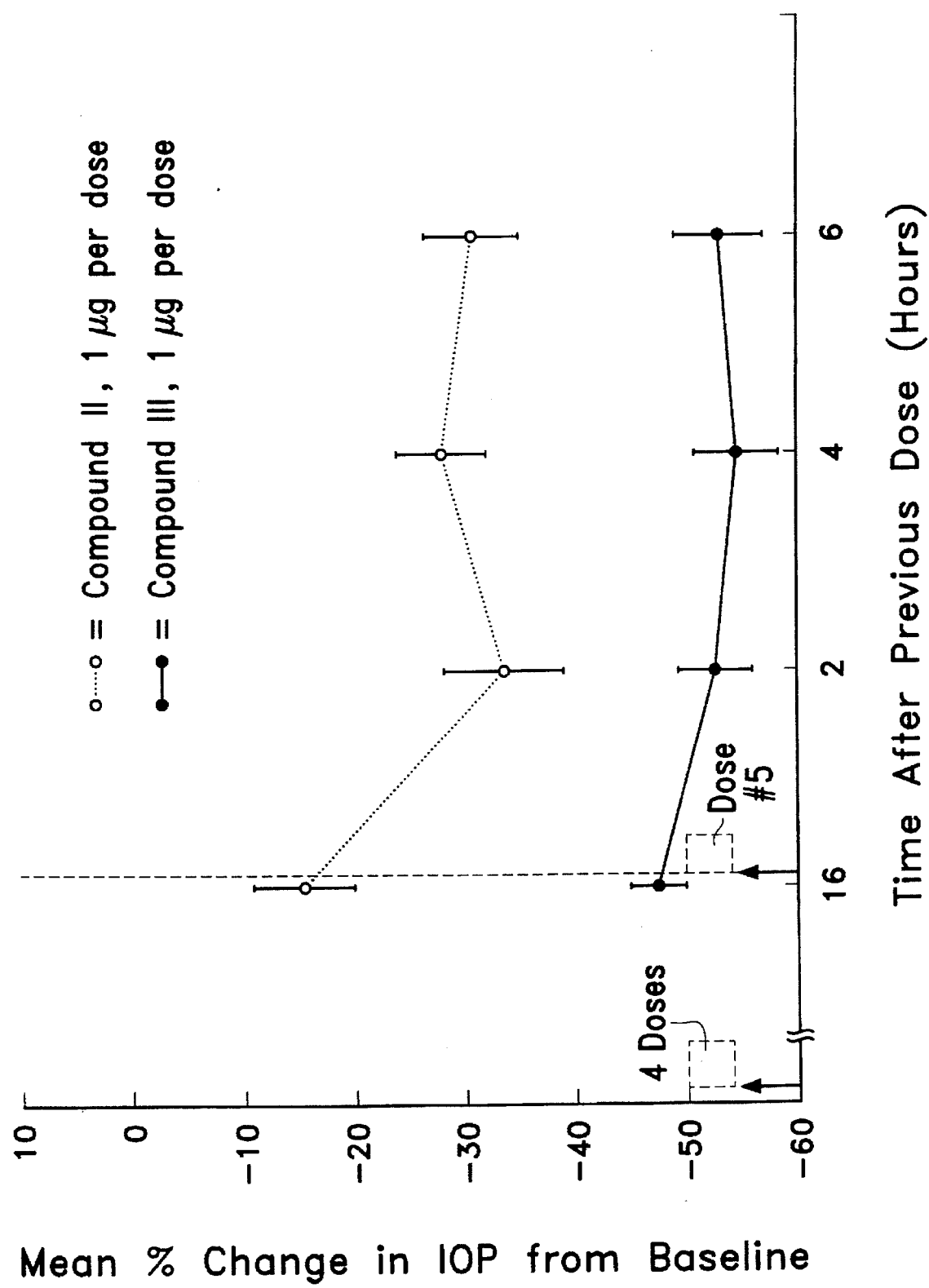

USE OF CERTAIN 9-HALOPROSTAGLANDINS TO TREAT GLAUCOMA AND OCULAR HYPERTENSION

CROSS REFERENCE TO RELATED APPLICATION

This application is a continuation of U.S. patent application Ser. No. 08/167,747, filed Dec. 15, 1993, now abandoned.

BACKGROUND OF THE INVENTION

The present invention relates to the use of prostaglandins and prostaglandin analogues for the treatment of glaucoma and ocular hypertension. As used herein, the terms "prostaglandin" and "PG" shall refer to prostaglandins and derivatives and analogues thereof, except as otherwise indicated by context. Naturally-occurring prostaglandins, including prostaglandins of the F series (such as $PGF_{2\alpha}$), the E series (such as $PGE_2$) and the D series (such as $PGD_2$), are known to lower intraocular pressure (IOP) after topical ocular instillation, but can cause marked conjunctival hyperemia and/or inflammation with a number of associated side effects.

Hyperemia refers to vasodilation of conjunctival blood vessels, giving the eye a so-called "blood-shot" appearance. Prostaglandins may produce hyperemia directly through their pharmacological action on the vessels, which is undesirable due to its unattractive cosmetic appearance. Aside from its unattractive appearance, this type of hyperemia is usually without other signs and symptoms, and is of a benign nature. Prostaglandins may also produce hyperemia indirectly through production or exacerbation of inflammation in conjunctival tissues. In inflammation, other side effects such as conjunctival edema, cellular infiltration, itching, burning or foreign body sensation are typically present. Hyperemia associated with inflammation is of greater concern clinically, since edema and inflammatory cellular infiltration can produce pathologic changes of the conjunctival tissue and other mediators may become involved. There is therefore a clear distinction between the mechanisms of these two types of hyperemia: one being a benign type of vasodilation with no lasting consequences to patient; and the other being an irritative phenomenon which may result in tissue changes and discomfort.

The intolerable side effects associated with PGE's and PGF's stem from inflammation. Prostaglandins of the D series are also well-known for causing inflammation with associated hyperemia. This phenomenon has extended to D series analogues, such as BW245C. See, for example, Nakajima, M. et al. "Effects of prostaglandin $D_2$ and its analogue, BW245C, on intraocular pressure in humans," *Graefe's Arch. Clin. Exp. Ophthalmol.*, 229:411–413 (1991).

Woodward (U.S. Pat. No. 5,093,329) has attempted to overcome these side effects while maintaining the IOP-lowering effect; however, Woodward's data demonstrate only a brief IOP-lowering effect of these compounds in rabbits. In a subsequently published study, Crawford et al. (*J. Glaucoma*, 1:94–99 (1992)) found that SQ27986 (a compound of the type disclosed by Woodward) produces an initial IOP increase, but no significant IOP decrease, in normotensive monkeys.

SUMMARY OF THE INVENTION

It has now been unexpectedly discovered that certain D series analogues are significantly more effective in lowering IOP than other, known prostaglandins. In particular, the 9-haloprostaglandins of the present invention have unexpectedly been found to lower IOP to a greater degree than other known PGs and without the side effects typically associated with inflammation which often accompany topical ocular administration of D series prostaglandins.

BRIEF DESCRIPTION OF THE DRAWING

FIG. 1 graphically illustrates the results of the study presented in Example 2.

DETAILED DESCRIPTION OF THE INVENTION

The 9-haloprostaglandins which are useful in the compositions of the present invention have the general formula:

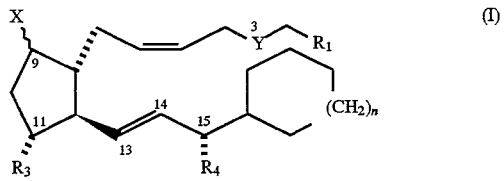

wherein:

$R_1 = CO_2R_2$, wherein $R_2 = H$, a cationic salt moiety, or an ophthalmically acceptable ammonium moiety; or $R_1$ may also represent an ophthalmically acceptable ester moiety;

X=halogen, particularly Cl or F, in either configuration;

$Y = CH_2$ or O;

$R_3$, $R_4$ can be the same or different, and are selected from: free or functionally modified hydroxy groups; and n=0 or 1.

As used in this specification, the term "ophthalmically acceptable ester moiety" refers to an ophthalmically acceptable ester moiety which hydrolyzes to the parent acid upon topical delivery to the eye. Examples of ophthalmically acceptable esters include, but are not limited to: $R_2$=substituted or unsubstituted alkyl, cycloalkyl, (cycloalkyl)alkyl, aryl, arylalkyl, heteroaryl, or (heteroaryl)alkyl, wherein substituents include alkyl, halo, a free or functionally modified hydroxy group, or a free or functionally modified thiol. As used in this specification, the term "heteroaryl" refers to a monocyclic ring system of 5 or 6 atoms composed of C, N, O, and/or S, such as furan, thiophene, pyrrole, pyrazole, imidazole, triazole, tetrazole, oxazole, isothiazole, thiazole, thiadiazole, pyridine, pyrimidine, pyradazine and pyrazine. Similarly, $R_3$ and $R_4$ represent either free hydroxy groups or acylated (esterified) hydroxy groups which hydrolyze to the parent hydroxy groups upon topical delivery to the eye.

It is preferred to use compounds of formula (I) wherein: $R_1=CO_2R_2$; $R_2=H$, methyl, ethyl, n-propyl, isopropyl, t-butyl or benzyl; X=Cl in the β (R) configuration; Y=O or $CH_2$; $R_3$ and $R_4$=OH; and n=1. It is most preferred to use compounds of formula (I) wherein: $R_1=CO_2R_2$; $R_2=H$, methyl, ethyl, isopropyl or t-butyl; X=Cl in the β (R) configuration; Y=O; $R_3$ and $R_4$=OH; and n=1.

Examples of preferred compounds are:

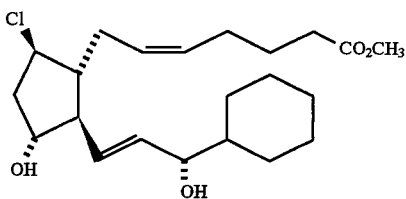

(5Z, 13E)-(9R, 11R, 15S)-9-Chloro-15-cyclohexyl-11,15-dihydroxy-16,17,18,19,20-pentanor-5,13-prostadienoic Acid Methyl Ester

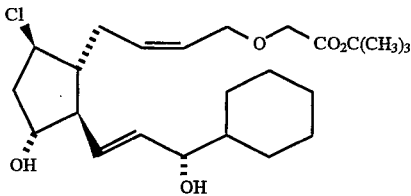

(5Z, 13E)-(9R, 11 R 15S)-9-Chloro-15-cyclohexyl-11,15-dihydroxy-3-oxa-16,17,18,19,20-pentanor-5,13-prostadienoic Acid t-Butyl Ester The above-mentioned prostaglandins are disclosed in U.S. Pat. No. 5,004,752 (Raduechel et al.) and EP 299 91 4 (Buchmann et al.). As these patents also disclose methods of synthesis of such compounds, the synthetic method will not be further discussed herein. To the extent that U.S. Pat. No. 5,004,752 and EP 299 914 teach the synthesis of the prostaglandins of the present invention, these patents are hereby incorporated by reference herein.

The compounds of formula (I) are useful in lowering intraocular pressure and thus are useful in the treatment of glaucoma. The preferred route of administration is topical. The dosage range for topical administration is generally between about 0.001 and about 1000 micrograms per eye (μg/eye) and is preferably between about 0.01 and about 100 μg/eye and most preferably between about 0.05 and 50 μg/eye. The compounds of the present invention can be administered as solutions, suspensions, or emulsions (dispersions) in a suitable ophthalmic vehicle.

In forming compositions for topical administration, the compounds of the present invention are generally formulated as between about 0.00002 to about 0.5 percent by weight (wt%) solutions in water at a pH between about 4.5 and about 8.0. The compounds are preferably formulated as between about 0.0001 to about 0.1 wt% and, most preferably, between about 0.001 and about 0.05 wt%. While the precise regimen is left to the discretion of the clinician, it is recommended that the compositions be topically applied by placing one or more drops in each eye one or more times a day.

Other ingredients which may be desirable to use in the ophthalmic preparations of the present invention include preservatives, co-solvents and viscosity building agents.

Antimicrobial Preservatives

Ophthalmic products are typically packaged in multidose form, which generally require the addition of preservatives to prevent microbial contamination during use. Suitable preservatives include: benzalkonium chloride, thimerosal, chlorobutanol, methyl paraben, propyl paraben, phenylethyl alcohol, edetate disodium, sorbic acid, ONAMER M®, or other agents known to those skilled in the art. Such preservatives are typically employed at a concentration between about 0.001 and about 1.0 wt%.

Co-Solvents

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; Tyloxapol; Cremophor EL; sodium dodecyl sulfate; glycerol; PEG 400; propylene glycol; cyclodextrins; or other agents known to those skilled in the art. Such co-solvents are typically employed at a concentration between about 0.01 and about 2 wt%.

Viscosity Agents

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include: polyvinyl alcohol; polyvinyl pyrrolidone; cellulosic polymers, such as methyl cellulose, hydroxy propyl methylcellulose, hydroxyethyl cellulose, carboxymethyl cellulose, hydroxy propyl cellulose; carboxy vinyl polymers, such as carbomer 910, carbomer 940, carbomer 934P and carbomer 1342; or other agents known to those skilled in the art. Such agents are typically used at a concentration between about 0.01 and about 2 wt%.

EXAMPLE 1

The following Formulations A–D are representative pharmaceutical compositions of the invention for topical use in lowering of intraocular pressure. Each of Formulations A–D may be formulated in accordance with procedures known to those skilled in the art.

| Ingredient | Amount (wt %) |
| --- | --- |
| Formulation A: | |
| Compound (III) | 0.002 |
| Dextran 70 | 0.1 |
| Hydroxypropyl methylcellulose | 0.3 |
| Sodium chloride | 0.77 |
| Potassium chloride | 0.12 |
| Disodium EDTA (Edetate disodium) | 0.05 |
| Benzalkonium chloride | 0.01 |
| Polysorbate 80 | 0.1 |
| HCl and/or NaOH | pH 7.2–7.5 |
| Purified water | q.s. to 100% |
| Formulation B: | |
| Compound (II) | 0.01 |
| Dextran 70 | 0.1 |
| Hydroxypropyl methylcellulose | 0.5 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Tyloxapol | 0.1 |
| Benzalkonium chloride | 0.01 |
| NaOH and/or HCl | pH 7.3–7.4 |
| Purified water | q.s. to 100% |
| Formulation C: | |
| Formula (I), wherein: $R_1 = CO_2R_2$, $R_2 = H$, $X = \beta(R)Cl$, $Y = O$, $R_3 = R_4 = OH$, and $n = 1$ | 0.05 |
| Monobasic sodium phosphate | 0.05 |
| Dibasic sodium phosphate (anhydrous) | 0.15 |

-continued

| Ingredient | Amount (wt %) |
| --- | --- |
| Sodium Chloride | 0.5 |
| Hydroxypropyl-β-cyclodextrin | 1.0 |
| Benzalkonium chloride | .01 |
| NaOH and/or HCl | pH 6.3–6.6 |
| Purified water | q.s. to 100% |
| Formulation D: | |
| Formula (I), wherein: $R_1 = CO_2R_2$, $R_2 = H$, $X = \beta(R)Cl$, $Y = CH_2$, $R_3 = R_4 = OH$, and $n = 0$ | 0.1 |
| Monobasic sodium phosphate | .05 |
| Dibasic sodium phosphate (anhydrous) | .15 |
| Sodium chloride | 0.6 |
| Tyloxapol | 0.4 |
| Benzalkonium chloride | .02 |
| NaOH and/or HCl | pH 6.3–6.6 |
| Purified water | q.s. to 100% |

EXAMPLE 2

The ability of certain compounds of the present invention to reduce intraocular pressure (IOP) was evaluated in cynomolgus monkeys with ocular hypertension produced by previous laser trabeculoplasty in the right eye. Animals had been trained to sit in restraint chairs and conditioned to accept experimental procedures without chemical restraint. IOP was determined with a pneumatonometer after light corneal anesthesia with dilute proparacaine. The test protocol included a treatment regimen consisting of 5 divided doses administered over a period of 2 and ½ days. Doses 2–5 were given 8, 24, 32 and 48 hours after the initial dose. Baseline IOP values were determined prior to treatment with the test formulation, and then IOP was determined 16 hours after the fourth dose, and 2, 4 and 6 hours after the fifth dose. Prostaglandin doses are micrograms of compound contained in each treatment.

The two tested compounds are the previously identified Compounds (II) and intraocular pressure. No indications of inflammation were observed during these studies.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma and ocular hypertension which comprises topically administering to the affected eye a therapeutically effective amount of a compound of formula:

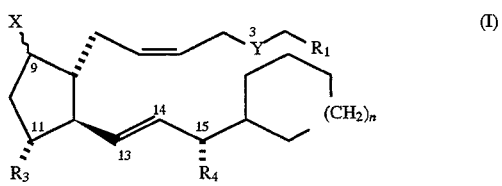

wherein:

$R_1 = CO_2R_2$, wherein $R_2 = H$, a cationic salt moiety, or an ophthalmically acceptable ammonium moiety; or $R_1$ may also represent an ophthalmically acceptable ester moiety;

X = halogen in either configuration;

Y = O;

$R_3$, $R_4$ can be the same or different, and are selected from: free or functionally modified hydroxy groups; and n = 0 or 1.

2. The method of claim 1, wherein: $R_1 = CO_2R_2$; $R_2$ = substituted or unsubstituted alkyl, cycloalkyl, (cycloalkyl)alkyl, aryl, arylalkyl, wherein substituents are selected from the group consisting of:

alkyl, halogen, a free or functionally modified hydroxy group, or a free or functionally modified thiol; and X = F or Cl in either configuration.

TABLE 1

| Compound | PG Dose | Baseline IOP (mm Hg) | Percent IOP Reduction at Hours after Dose/Dose # | | | |
| --- | --- | --- | --- | --- | --- | --- |
| | | | 16/4 | 2/5 | 4/5 | 6/5 |
| (II) | 1 µg | 31.1 | 15.6 ± 4.7 | 33.7 ± 5.5 | 28.1 ± 4.1 | 31.0 ± 4.6 |
| (III) | 1 µg | 31.3 | 47.6 ± 2.6 | 52.8 ± 3.3 | 54.7 ± 3.8 | 53.1 ± 4.1 |

Results are presented in Table 1, above, and in FIG. 1. Compounds (II) and (III) produced significant reduction of intraocular pressure at doses which are marginal or ineffective for other prostaglandins in published clinical studies. Compound (III) was especially potent, producing greater than 50% reduction of intraocular pressure with just 1 µg of compound. In contrast, Nakajima et al. (Graefe's Arch. Clin. Exp. Ophthalmol., 229:411–413 (1991)) reported that 50 µg of $PGD_2$ and 2.5 µg of BW245C (a $PGD_2$ analogue) reduce intraocular pressure in human eyes by 12% and 10%, respectively. Other studies (Woodward et al., Invest. Ophthalmol. Vis. Sci., 31:138–146 (1990)) reported for these reference compounds in rabbits describe a maximum IOP reduction of approximately 28% for 250 µg of $PGD_2$ and 22% for 25 µg of BW245C. These comparisons indicate the unexpected potency of Compounds (II) and (III) in reducing 3. The method of claim 2, wherein: $R_1 = CO_2R_2$; $R_2 = H$, methyl, ethyl, n-propyl, isopropyl, t-butyl or benzyl; X=Cl in the β (R) configuration; $R_3$ and $R_4$=OH; and n=1.

4. The method of claim 3, wherein: $R_2$=t-butyl.

5. The method of claim 1, wherein between about 0.001 and about 1000 micrograms of a compound of formula (I) is administered.

6. The method of claim 5, wherein between about 0.01 and about 100 micrograms of a compound of formula (I) is administered.

7. The method of claim 6, wherein between about 0.05 and about 50 micrograms of a compound of formula (I) is administered.

* * * * *

UNITED STATES PATENT AND TRADEMARK OFFICE
CERTIFICATE OF CORRECTION

PATENT NO.   :   5,627,209
DATED        :   May 6, 1997
INVENTOR(S)  :   DeSantis, Jr. et al.

It is certified that error appears in the above-identified patent and that said Letters Patent is hereby corrected as shown below:

Column 5, line 40, after "Compounds (II) and" insert --(III).--.

Column 5, line 53, replace "(11)" with --(II)--.

Signed and Sealed this

Twenty-first Day of October 1997

Attest:

BRUCE LEHMAN

Attesting Officer                Commissioner of Patents and Trademarks